(12) United States Patent
Inaba (10) Patent No.: US 12,290,276 B2
(45) Date of Patent: May 6, 2025

(54) MEDICAL DEVICE, CONTROL METHOD, AND COMPUTER-READABLE STORAGE MEDIUM

(71) Applicant: OLYMPUS CORPORATION, Tokyo (JP)

(72) Inventor: Kizuku Inaba, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 1054 days.

(21) Appl. No.: 17/204,348

(22) Filed: Mar. 17, 2021

(65) Prior Publication Data
US 2021/0196308 A1 Jul. 1, 2021

Related U.S. Application Data

(63) Continuation of application No. PCT/JP2018/034668, filed on Sep. 19, 2018.

(51) Int. Cl.
*A61B 17/32* (2006.01)
*A61B 18/14* (2006.01)

(52) U.S. Cl.
CPC ........... *A61B 17/320092* (2013.01); *A61B 2017/320082* (2017.08); *A61B 2017/320095* (2017.08);
(Continued)

(58) Field of Classification Search
CPC ........... A61B 18/1442; A61B 18/1445; A61B 18/1447; A61B 2018/145;
(Continued)

(56) References Cited

U.S. PATENT DOCUMENTS 9,878,183 B2 * 1/2018 Tanaka .............. A61B 18/1402
2013/0190660 A1 7/2013 Tanaka et al.
(Continued)

FOREIGN PATENT DOCUMENTS

WO 2013/042498 A1 3/2013
WO 2016/135977 A1 9/2016
(Continued)

OTHER PUBLICATIONS

Nov. 20, 2018 International Search Report issued in International Application No. PCT/JP2018/034668.

*Primary Examiner* — Daniel W Fowler
*Assistant Examiner* — Kyle M. Brown
(74) *Attorney, Agent, or Firm* — Oliff PLC (57) ABSTRACT

A medical device includes: a high-frequency power supply configured to output a high-frequency signal to an end effector; a first detection circuit configured to detect a first index value; a second detection circuit configured to detect a second index value; and a processor configured to execute a first mode in which an output value of the high-frequency signal from the high-frequency power supply is reduced, when a fluctuation of the first index value detected by the first detection circuit occurs and a fluctuation of the second index value detected by the second detection circuit occurs. The high-frequency power supply includes a power supply main body and an output circuit configured to output the high-frequency signal by converting power output from the power supply main body, and the first detection circuit is configured to detect a voltage of the power supply main body as the first index value.

18 Claims, 6 Drawing Sheets

(52) U.S. Cl.
CPC ....... *A61B 18/1442* (2013.01); *A61B 18/1445* (2013.01); *A61B 18/1447* (2013.01); *A61B 2018/145* (2013.01); *A61B 2018/146* (2013.01)

(58) Field of Classification Search
CPC .... A61B 2018/1452; A61B 2018/1455; A61B 2018/1457; A61B 2018/146; A61B 2018/1462; A61B 17/320092; A61B 2017/320082; A61B 2017/320095; A61B 2017/0003; A61B 2017/00017; A61B 17/320068
See application file for complete search history.

(56) References Cited

U.S. PATENT DOCUMENTS

| | | | |
|---|---|---|---|
| 2017/0000516 A1* | 1/2017 | Stulen | A61B 18/1445 |
| 2017/0164996 A1 | 6/2017 | Honda et al. | |
| 2017/0367754 A1 | 12/2017 | Narisawa | |
| 2018/0111009 A1 | 4/2018 | Tanaka et al. | |
| 2019/0046262 A1* | 2/2019 | Hayashida | A61B 18/18 |
| 2019/0105073 A1* | 4/2019 | Tanigami | A61B 17/320068 |
| 2019/0142489 A1 | 5/2019 | Hayashida et al. | |
| 2019/0274752 A1* | 9/2019 | Denzinger | A61B 17/320092 |
| 2023/0182172 A1* | 6/2023 | Kato | B06B 1/0284 |
| | | | 606/169 |

FOREIGN PATENT DOCUMENTS

| | | |
|---|---|---|
| WO | 2016/139872 A1 | 9/2016 |
| WO | 2017/187523 A1 | 11/2017 |
| WO | 2018/011858 A1 | 1/2018 |

* cited by examiner

MEDICAL DEVICE, CONTROL METHOD, AND COMPUTER-READABLE STORAGE MEDIUM

CROSS-REFERENCE TO RELATED APPLICATION

This application is a continuation of International Application No. PCT/JP2018/034668, filed on Sep. 19, 2018, the entire contents of which are incorporated herein by reference.

BACKGROUND

1. Technical Field

The present disclosure relates to a medical device, a control method, and a computer-readable storage medium.

2. Related Art

In the related art, there is known a medical device that applies high-frequency energy to a biological tissue from an end effector by outputting a high-frequency signal to be high-frequency power to the end effector (for example, see International Publication No. 2013/042498).

Here, in a case where an electroconductive member such as a metal forceps comes into contact with the end effector while treating the biological tissue, the high-frequency energy that should be used for the treatment of the biological tissue may be discharged, and treatment performance of the biological tissue may be deteriorated.

In addition, in the medical device described in International Publication No. 2013/042498, the presence or absence of contact between the end effector and the electroconductive member such as the metal forceps is detected by utilizing a fluctuation of the high-frequency signal output to the end effector.

SUMMARY

In some embodiments, a medical device includes: a high-frequency power supply configured to output a high-frequency signal to an end effector configured to apply high-frequency energy to treat a biological tissue; a first detection circuit configured to detect a first index value that is an indication of an output state of the high-frequency signal by the high-frequency power supply; a second detection circuit configured to detect a second index value that is an indication of a mechanical load applied to the end effector; and a processor configured to execute a first mode in which an output value of the high-frequency signal from the high-frequency power supply is reduced, when a fluctuation of the first index value detected by the first detection circuit occurs and a fluctuation of the second index value detected by the second detection circuit occurs. The high-frequency power supply includes a power supply main body and an output circuit configured to output the high-frequency signal by converting power output from the power supply main body, and the first detection circuit is configured to detect a voltage of the power supply main body as the first index value.

In some embodiments, provided is a control method executed by a processor of a medical device. The control method includes: monitoring, as a first index value, a voltage of a power supply main body of a high-frequency power supply, the first index value being an indication of an output state of a high-frequency signal output to an end effector by converting power output from the power supply main body; monitoring a second index value that is an indication of a mechanical load applied to the end effector; and reducing an output value of the high-frequency signal from the high-frequency power supply, when a fluctuation of the first index value occurs and a fluctuation of the second index value occurs.

In some embodiments, provided is a non-transitory computer-readable storage medium for storing a control program. The control program causes a processor of a medical device to: monitor, as a first index value, a voltage of a power supply main body of a high-frequency power supply, the first index value being an indication of an output state of a high-frequency signal output to an end effector by converting power output from the power supply main body; monitor a second index value that is an indication of a mechanical load applied to the end effector; and reduce an output value of the high-frequency signal from the high-frequency power supply, when a fluctuation of the first index value occurs and a fluctuation of the second index value occurs.

The above and other features, advantages and technical and industrial significance of this disclosure will be better understood by reading the following detailed description of presently preferred embodiments of the disclosure, when considered in connection with the accompanying drawings.

DETAILED DESCRIPTION

Hereinafter, embodiments of the disclosure will be described with reference to the drawings. Note that the disclosure is not limited to the embodiments described below. Further, in the description of the drawings, the same components will be denoted by the same reference numerals.

First Embodiment

Schematic Configuration of Medical System

Figure 1:
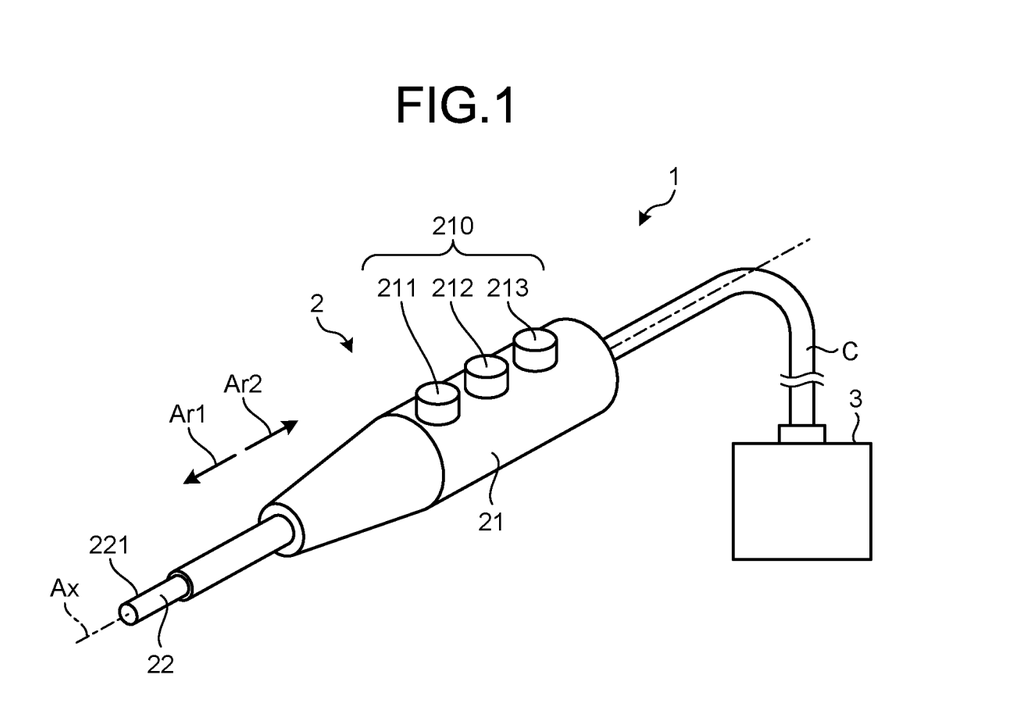
FIG. 1 is a diagram illustrating a medical system according to a first embodiment.
Figure 2:
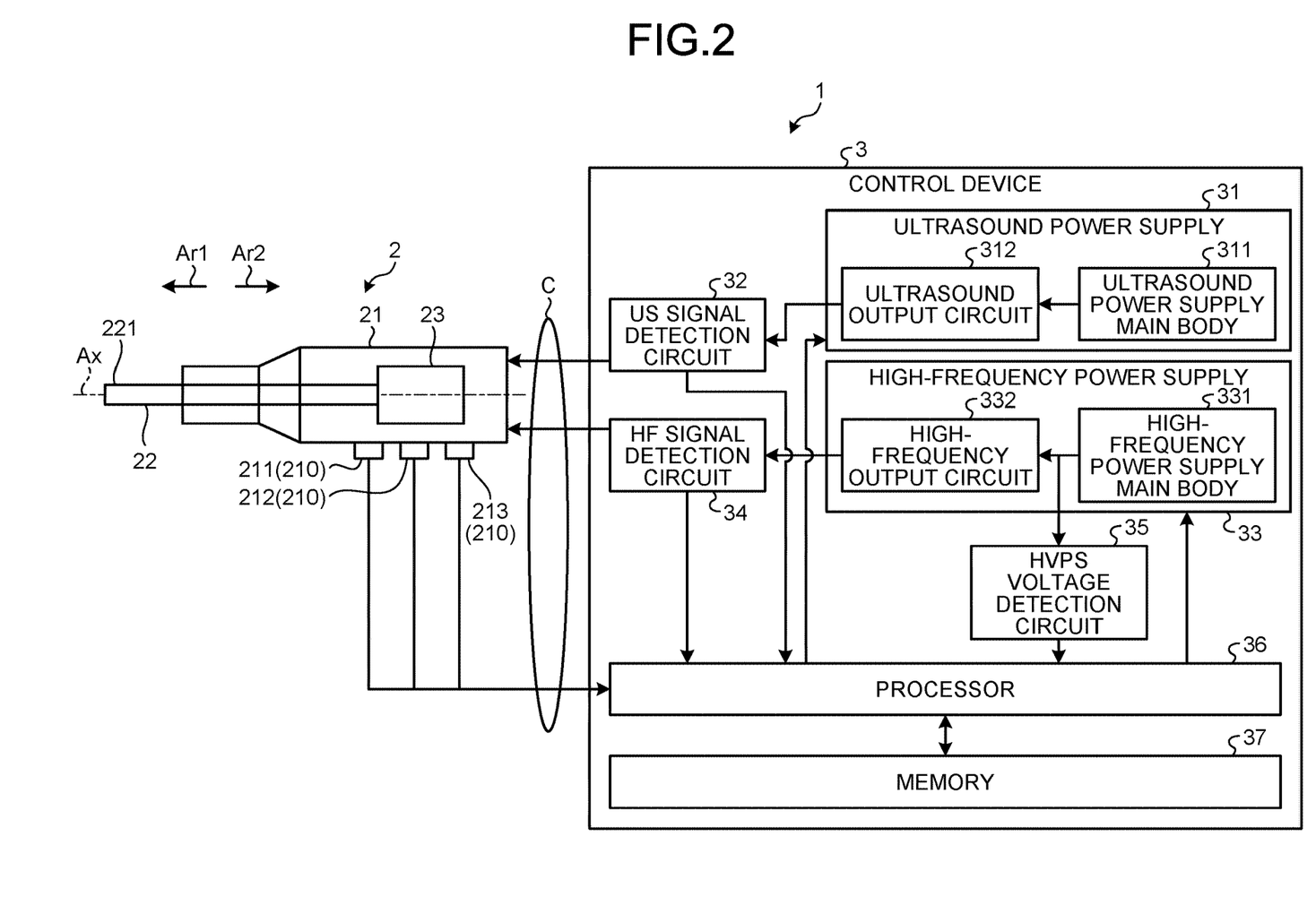
FIG. 2 is a diagram illustrating internal configurations of a treatment tool and a control device.

FIG. 1 is a diagram illustrating a medical system 1 according to a first embodiment. FIG. 2 is a diagram illustrating internal configurations of a treatment tool 2 and a control device 3.

The medical system 1 applies ultrasound energy and high-frequency energy to a treatment target site (hereinafter, referred to as the target site) in a biological tissue, thereby treating the target site. Note that treatments that can be performed by the medical system 1 according to the first embodiment are three treatments, that is, a first treatment that performs both coagulation and incision of the target site, a second treatment that performs only the coagulation of the target site, and a third treatment that performs only the incision of the target site. The medical system 1 includes a treatment tool 2 and a control device 3, as illustrated in FIG. 1 or 2.

Configuration of Treatment Tool

As illustrated in FIG. 1 or 2, the treatment tool 2 includes a housing 21, an ultrasound probe 22, and an ultrasound transducer 23.

In the following, one side of the ultrasound probe 22 along a center axis Ax is referred to as the distal end side Ar1 (FIGS. 1 and 2), and the other side is referred to as the proximal end side Ar2 (FIGS. 1 and 2).

The housing 21 has a substantially cylindrical shape extending along the center axis Ax and supports the ultrasound probe 22 and the ultrasound transducer 23.

As illustrated in FIG. 1 or 2, the housing 21 is provided with an interface 210 that is exposed to the outside and receives setting operations of a coagulation/incision mode, a coagulation mode, and an incision mode by an operator. The interface 210 includes first to third switches 211 to 213.

The first switch 211 receives the setting operation of the coagulation/incision mode by the operator. Then, the first switch 211 outputs an operation signal according to the setting operation to the control device 3 via an electric cable C (FIGS. 1 and 2) that electrically connects the treatment tool 2 and the control device 3.

The second switch 212 receives the setting operation of the coagulation mode by the operator. Then, the second switch 212 outputs an operation signal according to the setting operation to the control device 3 via the electric cable C.

The third switch 213 receives the setting operation of the incision mode by the operator. Then, the third switch 213 outputs an operation signal according to the setting operation to the control device 3 via the electric cable C.

The ultrasound probe 22 has an elongated shape extending along the center axis Ax and is made of an electroconductive material. In the ultrasound probe 22, an end 221 (FIGS. 1 and 2) of the distal end side Ar1 is mounted in the housing 21, in a state in which the end 221 is exposed to the outside. Further, in the ultrasound probe 22, an end of the proximal end side Ar2 is connected to a BLT (bolt-tightened Langevin type transducer) forming the ultrasound transducer 23. Then, the ultrasound probe 22 transmits the ultrasound vibration generated by the BLT from the end of the proximal end side Ar2 to the end 221 of the distal end side Ar1. The end 221 corresponds to an end effector according to the disclosure.

The ultrasound transducer 23 is inserted into the housing 21 from the proximal end side Ar2 of the housing 21 and is detachably configured with respect to the housing 21. Although the specific illustration is omitted, the ultrasound transducer 23 includes a BLT that generates the ultrasound vibration in response to the supply of a drive signal which is AC power.

Configuration of Control Device

The control device 3 corresponds to a medical device according to the disclosure. The treatment tool 2 is detachably connected to the control device 3 by the electric cable C. Then, the control device 3 generally controls the operation of the treatment tool 2 via the electric cable C. As illustrated in FIG. 2, the control device 3 includes an ultrasound power supply 31, a US signal detection circuit 32, a high-frequency power supply 33, an HF signal detection circuit 34, an HVPS voltage detection circuit 35, a processor 36, and a memory 37.

The ultrasound power supply 31 outputs a drive signal to the BLT forming the ultrasound transducer 23 via the electric cable C, under the control of the processor 36. As illustrated in FIG. 2, the ultrasound power supply 31 includes an ultrasound power supply main body 311 and an ultrasound output circuit 312.

The ultrasound power supply main body 311 is a source power supply of the ultrasound power supply 31.

Under the control of the processor 36, the ultrasound output circuit 312 converts (boosts or the like) power output from the ultrasound power supply main body 311 and outputs a drive signal to the BLT forming the ultrasound transducer 23 via the electric cable C.

The US signal detection circuit 32 detects a US signal on the basis of the drive signal output from the ultrasound power supply 31 (ultrasound output circuit 312) to the BLT forming the ultrasound transducer 23. Then, the US signal detection circuit 32 outputs the detected US signal to the processor 36.

Here, examples of the US signal can include a voltage phase signal in the drive signal (hereinafter, referred to as a US voltage phase signal), a current phase signal in the drive signal (hereinafter, referred to as a US current phase signal), a current value in the drive signal (hereinafter, referred to as a US current), a voltage value in the drive signal (hereinafter, referred to as a US voltage), an impedance value calculated from the US current and the US voltage (hereinafter, referred to as a US impedance), and the like.

The US impedance is a value serving as an indication of a mechanical load applied to the ultrasound probe 22 (end 221) and corresponds to a second index value according to the disclosure. That is, the US signal detection circuit 32 corresponds to a second detection circuit according to the disclosure. Further, the US signal corresponds to a second detection signal according to the disclosure.

The high-frequency power supply 33 outputs a high-frequency signal to be high-frequency power between the ultrasound probe 22 and a counter electrode plate (not illustrated) attached to a surface of a subject via the electric cable C, under the control of the processor 36. The high-frequency power supply 33 includes a high-frequency power supply main body 331 and a high-frequency output circuit 332.

The high-frequency power supply main body 331 is a source power supply of the high-frequency power supply 33 and corresponds to a power supply main body according to the disclosure.

The high-frequency output circuit 332 corresponds to an output circuit according to the disclosure. Under the control of the processor 36, the high-frequency output circuit 332 converts (boosts or the like) power output from the high-frequency power supply main body 331 and outputs a high-frequency signal between the ultrasound probe 22 and the counter electrode plate (not illustrated) via the electric cable C.

The HF signal detection circuit 34 detects an HF signal on the basis of the high-frequency signal output between the ultrasound probe 22 and the counter electrode plate (not illustrated) from the high-frequency power supply 33 (high-frequency output circuit 332). Then, the HF signal detection circuit 34 outputs the detected HF signal to the processor 36.

Here, examples of the HF signal can include a voltage phase signal in the high-frequency signal (hereinafter, referred to as an HF voltage phase signal), a current phase signal in the high-frequency signal (hereinafter, referred to as an HF current phase signal), a current value in the high-frequency signal (hereinafter, referred to as an HF current), a voltage value in the high-frequency signal (hereinafter, referred to as an HF voltage), an impedance value calculated from the HF current and the HF voltage (hereinafter, referred to as an HF impedance), a resistance calculated from the HF current and the HF voltage (hereinafter, referred to as an HF resistance), and the like.

The HVPS voltage detection circuit 35 detects a voltage value (hereinafter, referred to as an HVPS voltage) in power output from the high-frequency power supply main body 331 to the high-frequency output circuit 332. Then, the HVPS voltage detection circuit 35 outputs a detection signal according to the HVPS voltage to the processor 36.

The HVPS voltage is a value serving as an indication of an output state of the high-frequency signal by the high-frequency power supply 33 and corresponds to a first index value according to the disclosure. That is, the HVPS voltage detection circuit 35 corresponds to a first detection circuit according to the disclosure. Further, the detection signal output from the HVPS voltage detection circuit 35 to the processor 36 corresponds to a first detection signal according to the disclosure.

The processor 36 is, for example, a central processing unit (CPU), a field-programmable gate array (FPGA), or the like, and controls the operation of the entire medical system 1 according to a program stored in the memory 37.

Note that functions of the processor 36 will described in the following "control method".

The memory 37 is a semiconductor memory such as a random access memory (RAM) and a read only memory (ROM), and stores a program executed by the processor 36, information necessary for processing of the processor 36, and the like. Note that the program executed by the processor 36 may be stored in an external recording medium such as a flash memory, a hard disk drive (HDD), a magneto-optical (MO) disk, a writable compact disk (CD-R), and a writable digital versatile disk (DVD-R), and may be downloaded to the memory 37 by a corresponding input/output device. Further, the program executed by the processor 36 may be stored in a network server, for example, and may be downloaded to the memory 37 via the Internet, a local area network (LAN), or the like.

Control Method

Next, a control method executed by the processor 36 will be described.

Figure 3:
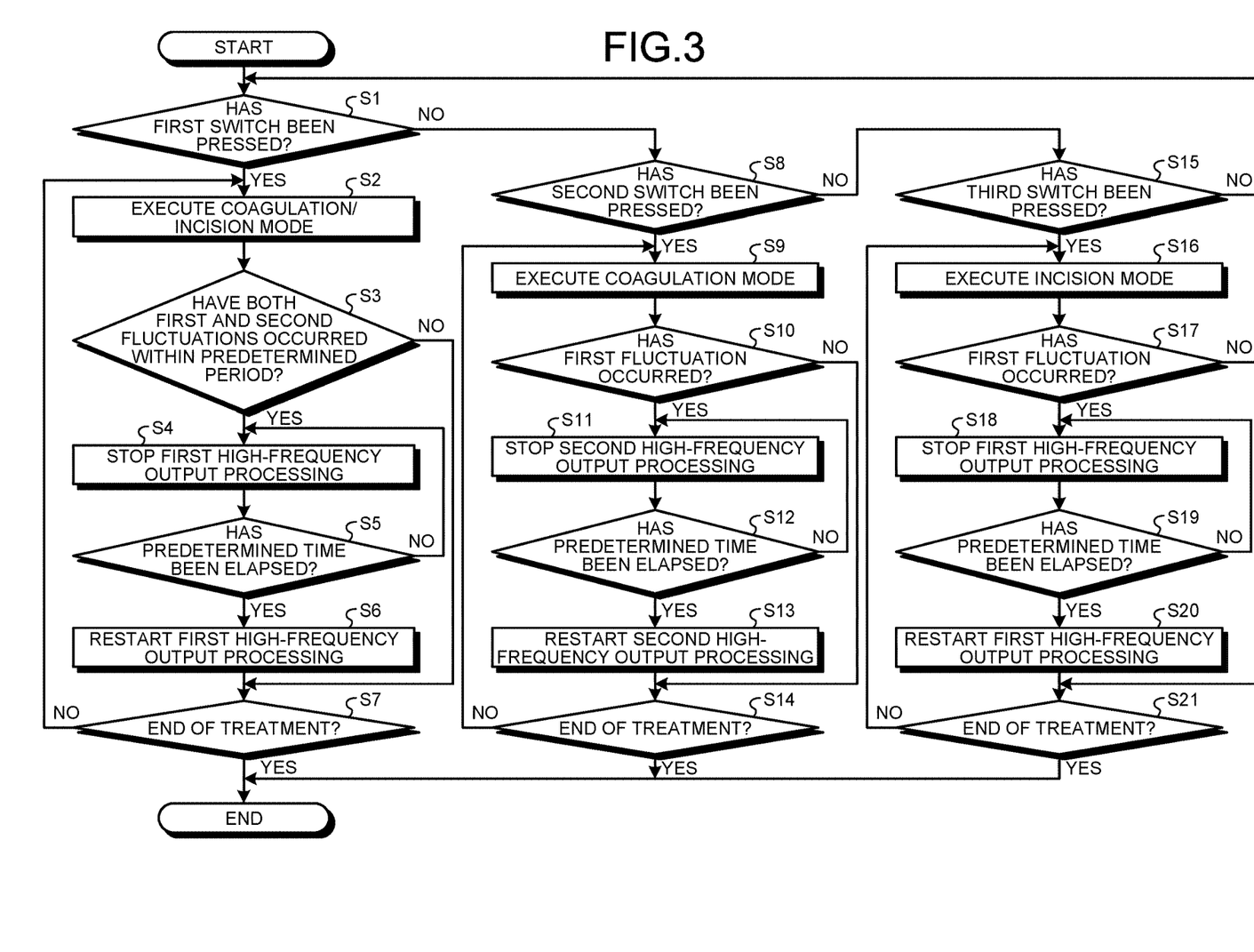
FIG. 3 is a flowchart illustrating a control method executed by a processor.

FIG. 3 is a flowchart illustrating the control method.

The operator holds the treatment tool 2 by hands and brings the end 221 of the distal end side Ar1 of the ultrasound probe 22 into contact with the target site. Then, when the first treatment is performed, the operator presses the first switch 211 (step S1: Yes).

When the first switch 211 is pressed (step S1: Yes), the processor 36 executes the coagulation/incision mode (step S2).

The coagulation/incision mode is a mode in which the first treatment is performed, and is a mode in which ultrasound energy and high-frequency energy are applied to the target site substantially at the same time. The coagulation/incision mode corresponds to a combined treatment mode according to the disclosure.

Here, in the coagulation/incision mode, when the ultrasound energy is applied to the target site, the processor 36 executes ultrasound output processing illustrated below.

Specifically, the processor 36 controls the operation of the ultrasound output circuit 312, sweeps a frequency in the drive signal output from the ultrasound output circuit 312, and searches for a resonance frequency of the BLT forming the ultrasound transducer 23, on the basis of the US signal (for example, a phase difference between the US current, the US current phase signal, and the US voltage phase signal or the like) output from the US signal detection circuit 32. Then, the processor 36 controls the operation of the ultrasound output circuit 312, and executes PLL control that locks the frequency in the drive signal output from the ultrasound output circuit 312 to the searched resonance frequency, on the basis of the US signal (for example, a phase difference between the US current phase signal and the US voltage phase signal or the like). As a result, the BLT forming the ultrasound transducer 23 generates a longitudinal vibration (ultrasound vibration) to be a vibration in a direction along the center axis Ax. Further, the end 221 of the distal end side Ar1 of the ultrasound probe 22 vibrates with a desired amplitude due to the longitudinal vibration. Then, the ultrasound vibration is applied to the target site from the end 221. In other words, ultrasound energy is applied to the target site from the end 221.

Further, in the coagulation/incision mode, when the high-frequency energy is applied to the target site, the processor 36 executes first high-frequency output processing illustrated below.

Specifically, the processor 36 controls the operation of the high-frequency output circuit 332, and sets the high-frequency signal output from the high-frequency output circuit 332 to predetermined power, on the basis of the HF signal output from the HF signal detection circuit 34. Then, the processor 36 continuously outputs the high-frequency signal set to the predetermined power from the high-frequency output circuit 332. As a result, a high-frequency current continuously flows through the target site. In other words, high-frequency energy is continuously applied to the target site.

Further, when the coagulation/incision mode is executed, the processor 36 executes the first mode illustrated below (steps S3 to S6).

Figure 4:
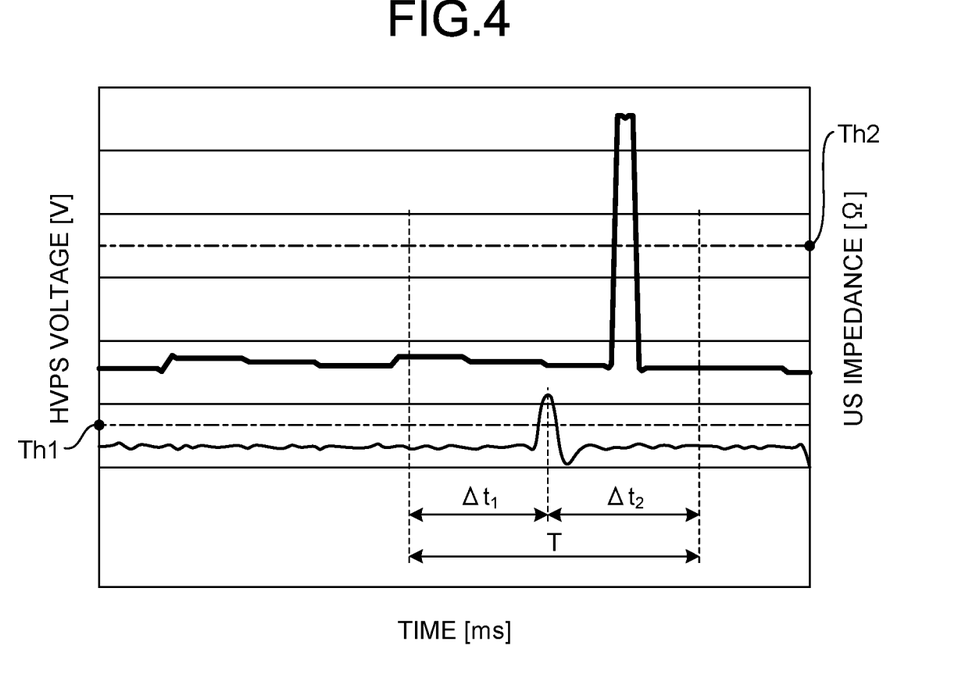
FIG. 4 is a diagram illustrating step S3 illustrated in FIG. 3.

FIG. 4 is a diagram illustrating step S3. Specifically, in FIG. 4, a horizontal axis represents a time [ms]. Further, a vertical axis represents each of an HVPS voltage [V] and a US impedance [Ω]. FIG. 4 illustrates a case where a first fluctuation occurs in the HVPS voltage and a second fluctuation occurs in the US impedance, within the predetermined period $T(\Delta t_1+\Delta t_2)$.

First, the processor 36 monitors each of the detection signal (HVPS voltage) output from the HVPS voltage detection circuit 35 and the US signal (US impedance) output from the US signal detection circuit 32. Then, the processor 36 determines whether or not the first fluctuation has occurred in the HVPS voltage and the second fluctuation has occurred in the US impedance, within the predetermined period $T(\Delta t_1+\Delta t_2)$ (step S3). Note that $\Delta t_1$ is, for example, a time of about 2 [ms]. Further, $\Delta t_2$ is a time of about 3 [ms] to 10 [ms]. That is, the predetermined period T is a period of about 5 [ms] to 12 [ms].

Here, when the HVPS voltage exceeds a specific first threshold Th1 (FIG. 4), the processor 36 determines that the first fluctuation has occurred in the HVPS voltage. The first threshold Th1 is, for example, a voltage value obtained by adding a specific voltage value to a normal HVPS voltage at the time of treatment of the target site. Further, when the US impedance exceeds a specific second threshold Th2 (FIG. 4), the processor 36 determines that the second fluctuation has occurred in the US impedance. The second threshold Th2 is, for example, an impedance value obtained by adding a specific impedance value to a normal US impedance at the time of treatment of the target site.

When it is determined that both the first and second fluctuations have occurred within the predetermined period T (step S3: Yes), the processor 36 stops the first high-frequency output processing (step S4). In other words, the processor 36 controls the operation of the high-frequency output circuit 332 and stops the output of the high-frequency signal from the high-frequency output circuit 332.

After step S4, the processor 36 determines whether or not a predetermined time has elapsed after the first high-frequency output processing is stopped in step S4 (step S5).

When it is determined that the predetermined time has not elapsed (step S5: No), the processor 36 returns to step S4. Then, the processor 36 continues to stop the first high-frequency output processing.

On the other hand, when it is determined that the predetermined time has elapsed (step S5: Yes), the processor 36 restarts the first high-frequency output processing (step S6).

When it is determined that at least one of the first and second fluctuations has not occurred within the predetermined period T (step S3: No) or after step S6, the processor 36 determines whether or not to end the treatment of the target site (step S7).

For example, when the operator operates the first switch 211 (treatment end instruction), when the elapsed time from execution of step S2 exceeds the predetermined time, or when various signals including errors are detected, the processor 36 determines "Yes" in step S7. For example, when the operator does not operate the first switch 211 (treatment end instruction), when the elapsed time from execution of step S2 does not exceed the predetermined time, or when various signals including errors are not detected, the processor 36 determines "No" in step S7.

When it is determined that the treatment of the target site is ended (step S7: Yes), the processor 36 ends the present control flow.

On the other hand, when it is determined that the treatment of the target site is continued (step S7: No), the processor 36 returns to step S2. Then, the processor 36 continues to execute the coagulation/incision mode.

When the second treatment is performed, the operator presses the second switch 212.

Then, when the second switch 212 is pressed (step S8: Yes), the processor 36 executes the coagulation mode (step S9).

The coagulation mode is a mode in which the second treatment is performed, and is a mode in which only high-frequency energy is applied to the target site. The coagulation mode corresponds to a single treatment mode according to the disclosure.

Here, in the coagulation mode, when the high-frequency energy is applied to the target site, the processor 36 executes second high-frequency output processing illustrated below.

Specifically, the processor 36 controls the operation of the high-frequency output circuit 332, and sets the high-frequency signal output from the high-frequency output circuit 332 to predetermined power, on the basis of the HF signal output from the HF signal detection circuit 34. Then, the processor 36 intermittently outputs a high-frequency signal set to a predetermined power from the high-frequency output circuit 332. As a result, a high-frequency current flows intermittently through the target site. In other words, high-frequency energy is intermittently applied to the target site.

Further, when the coagulation mode is executed, the processor 36 executes the second mode illustrated below (steps S10 to S13).

First, the processor 36 monitors the detection signal (HVPS voltage) output from the HVPS voltage detection circuit 35. Then, the processor 36 determines whether or not the first fluctuation has occurred in the HVPS voltage (step S10).

When it is determined that the first fluctuation has occurred (step S10: Yes), the processor 36 stops the second high-frequency output processing (step S11). In other words, the processor 36 controls the operation of the high-frequency output circuit 332 and stops the output of the high-frequency signal from the high-frequency output circuit 332.

After step S11, the processor 36 determines whether or not a predetermined time has elapsed after the second high-frequency output processing is stopped in step S11 (step S12).

When it is determined that the predetermined time has not elapsed (step S12: No), the processor 36 returns to step S11. Then, the processor 36 continues to stop the second high-frequency output processing.

On the other hand, when it is determined that the predetermined time has elapsed (step S12: Yes), the processor 36 restarts the second high-frequency output processing (step S13).

When it is determined that the first fluctuation has not occurred (step S10: No) or after step S13, the processor 36 determines whether or not to end the treatment of the target site (step S14).

For example, when the operator operates the second switch 212 (treatment end instruction), when the elapsed time from execution of step S9 exceeds the predetermined time, or when various signals including errors are detected, the processor 36 determines "Yes" in step S14. On the other hand, when the operator does not operate the second switch 212 (treatment end instruction), when the elapsed time from execution of step S9 does not exceed the predetermined time, or when various signals including errors are not detected, the processor 36 determines "No" in step S14.

When it is determined that the treatment of the target site is ended (step S14: Yes), the processor 36 ends the present control flow.

On the other hand, when it is determined that the treatment of the target site is continued (step S14: No), the processor 36 returns to step S9. Then, the processor 36 continues to execute the coagulation mode.

When the third treatment is performed, the operator presses the third switch 213 (step S15: Yes).

Then, when the third switch 213 is pressed (step S15: Yes), the processor 36 executes the incision mode (step S16).

The incision mode is a mode in which the third treatment is performed, and is a mode in which only high-frequency energy is applied to the target site. The incision mode corresponds to a single treatment mode according to the disclosure.

Here, in the incision mode, when the high-frequency energy is applied to the target site, the processor 36 executes the first high-frequency output processing.

Further, when the incision mode is executed, the processor 36 executes the second mode illustrated below (steps S17 to S20).

First, the processor 36 monitors the detection signal (HVPS voltage) output from the HVPS voltage detection circuit 35. Then, the processor 36 determines whether or not the first fluctuation has occurred in the HVPS voltage (step S17).

When it is determined that the first fluctuation has occurred (step S17: Yes), the processor 36 stops the first high-frequency output processing (step S18). In other words, the processor 36 controls the operation of the high-frequency output circuit 332 and stops the output of the high-frequency signal from the high-frequency output circuit 332.

After step S18, the processor 36 determines whether or not a predetermined time has elapsed after the first high-frequency output processing is stopped in step S18 (step S19).

When it is determined that the predetermined time has not elapsed (step S19: No), the processor 36 returns to step S18. Then, the processor 36 continues to stop the first high-frequency output processing.

On the other hand, when it is determined that the predetermined time has elapsed (step S19: Yes), the processor 36 restarts the first high-frequency output processing (step S20).

When it is determined that the first fluctuation has not occurred (step S17: No) or after step S20, the processor 36 determines whether or not to end the treatment of the target site (step S21).

For example, when the operator operates the third switch 213 (treatment end instruction), when the elapsed time from execution of step S16 exceeds the predetermined time, or when various signals including errors are detected, the processor 36 determines "Yes" in step S21. On the other hand, when the operator does not operate the third switch 213 (treatment end instruction), when the elapsed time from execution of step S16 does not exceed the predetermined time, or when various signals including errors are not detected, the processor 36 determines "No" in step S21.

When it is determined that the treatment of the target site is ended (step S21: Yes), the processor 36 ends the present control flow.

On the other hand, when it is determined that the treatment of the target site is continued (step S21: No), the processor 36 returns to step S16. Then, the processor 36 continues to execute the incision mode.

According to the first embodiment described above, the following effects are obtained.

In the control device 3 according to the first embodiment, the processor 36 monitors the detection signal (HVPS voltage) output from the HVPS voltage detection circuit 35 and the US signal (US impedance) output from the US signal detection circuit 32. Then, the processor 36 determines whether or not the first fluctuation has occurred in the HVPS voltage and the second fluctuation has occurred in the US impedance (step S3). Further, when both the first and second fluctuations occur, the processor 36 executes the first mode in which the output value of the high-frequency signal from the high-frequency power supply 33 is reduced (the output of the high-frequency signal from the high-frequency power supply 33 is stopped) (steps S3 to S6).

Here, when the electroconductive member such as the metal forceps comes into contact with the ultrasound probe (end 221), the resistance decreases, so that the HF current increases and the HF voltage decreases. Then, since the entire output increases, the source HVPS voltage increases. Further, when the electroconductive member such as the metal forceps comes into contact with the ultrasound probe 22 (end 221), the mechanical load applied to the ultrasound probe 22 increases, so that the US impedance increases.

That is, by using the two parameters of the HVPS voltage and the US impedance, the presence or absence of contact between the ultrasound probe 22 (end 221) and the electroconductive member such as the metal forceps can be detected with high accuracy. Further, when both the first and second fluctuations occur, that is, when the ultrasound probe 22 (end 221) and the electroconductive member such as the metal forceps come into contact with each other, the output value of the high-frequency signal from the high-frequency power supply 33 is reduced (the output of the high-frequency signal from the high-frequency power supply 33 is stopped). Therefore, it is possible to suppress the discharge of high-frequency energy due to the contact between the ultrasound probe 22 and the electroconductive member such as the metal forceps, and as a result, it is possible to suppress the deterioration of the treatment performance of the target site.

Incidentally, the contact time between the ultrasound probe 22 (end 221) and the electroconductive member such as the metal forceps is a finite time.

In the control device 3 according to the first embodiment, in the first mode, the processor 36 continues to stop the output of the high-frequency signal from the high-frequency power supply 33 for the specific period (steps S4 and S5), and after elapse of the specific period, the processor 36 restarts the output of the high-frequency signal from the high-frequency power supply 33 (step S6).

That is, when the discharge of high-frequency energy due to the contact between the ultrasound probe 22 and the electroconductive member such as the metal forceps does not occur, the output of the high-frequency signal from the high-frequency power supply 33 is restarted. Therefore, the treatment of the target site can be performed efficiently.

Incidentally, when the electroconductive member such as the metal forceps comes into contact with the ultrasound probe 22 (end 221), the first fluctuation of the HVPS voltage and the second fluctuation of the US impedance occur within the predetermined period T.

In the control device 3 according to the first embodiment, when both the first and second fluctuations occur within the predetermined period T (step S3: Yes), the processor 36 stops the output of the high-frequency signal from the high-frequency power supply 33 (step S4).

Therefore, the presence or absence of contact between the ultrasound probe 22 (end 221) and the electroconductive member such as the metal forceps can be detected with higher accuracy.

Second Embodiment

Next, a second embodiment will be described.

In the following description, the same components as those in the first embodiment will be denoted by the same reference numerals, and detailed description thereof will be omitted or simplified.

In the first embodiment described above, a US impedance is adopted as a second index value according to the disclosure.

On the other hand, in the second embodiment, a mechanical load applied to an ultrasound probe 22 is adopted as the second index value according to the disclosure.

Figure 5:
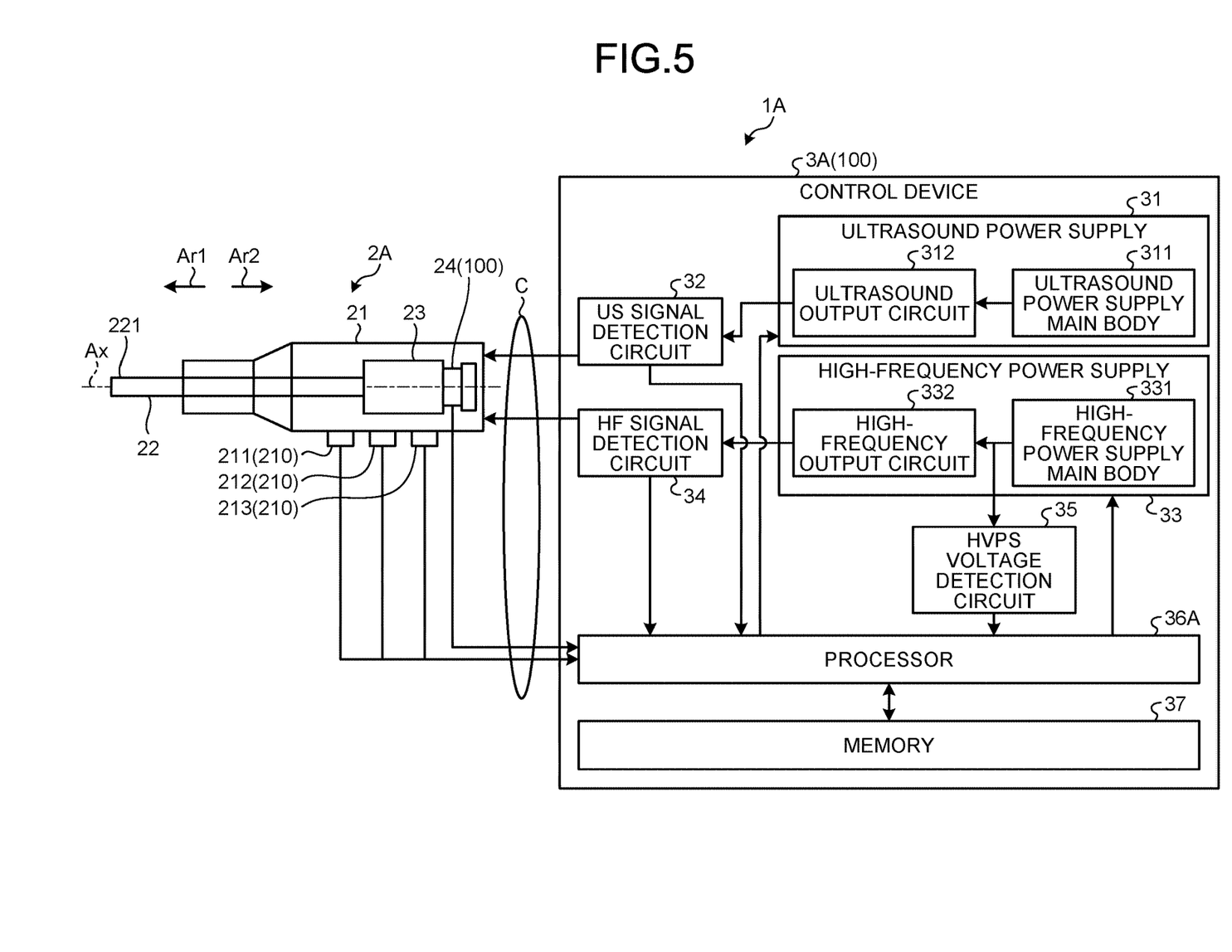
FIG. 5 is a diagram illustrating a medical system according to a second embodiment.

FIG. 5 is a diagram illustrating a medical system 1A according to the second embodiment.

Specifically, as illustrated in FIG. 5, the medical system 1A adopts a treatment tool 2A, which is a treatment tool 2 equipped with a force sensor 24, as compared with a medical system 1 described in the first embodiment.

The force sensor 24 is provided in a housing 21 and detects a mechanical load applied to an ultrasound probe 22. Then, the force sensor 24 outputs a detection signal according to the mechanical load to a control device 3A via an electric cable C. Note that an arrangement position of the force sensor 24 may be any position that can detect the mechanical load applied to the ultrasound probe 22.

The mechanical load corresponds to the second index value according to the disclosure. That is, the force sensor 24 corresponds to a second detection circuit according to the disclosure. Further, the detection signal output from the force sensor 24 to the control device 3A corresponds to a second detection signal according to the disclosure. Further, the force sensor 24 and the control device 3A correspond to a medical device 100 (FIG. 5) according to the disclosure.

With the adoption of the force sensor 24 described above, a processor 36A according to the second embodiment executes different processing only in step S3, as compared with a control method (FIG. 3) described in the first embodiment described above.

Figure 6:
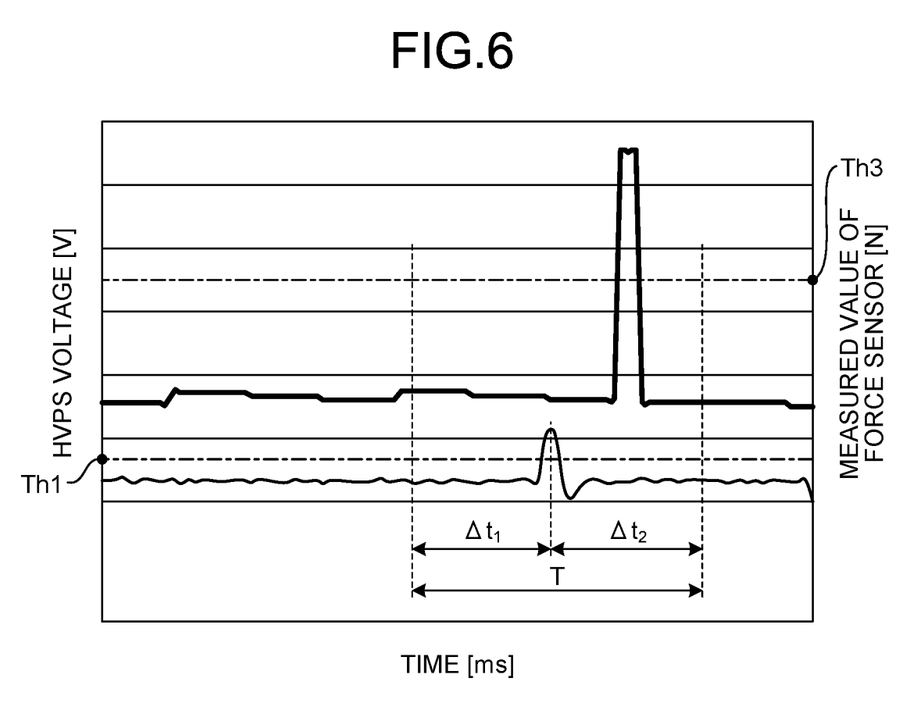
FIG. 6 is a diagram illustrating step S3 according to the second embodiment.

FIG. 6 is a diagram illustrating step S3 according to the second embodiment. Specifically, in FIG. 6, a horizontal axis represents a time [ms]. Further, a vertical axis represents each of an HVPS voltage [V] and a measured value [N] of the force sensor 24. FIG. 6 illustrates a case where a first fluctuation occurs in the HVPS voltage and a second fluctuation occurs in the measured value of the force sensor 24, within a predetermined period $T(\Delta t_1 + \Delta t_2)$.

Specifically, the processor 36A monitors the detection signal (HVPS voltage) output from an HVPS voltage detection circuit 35 and the detection signal (measured value of the force sensor 24) output from the force sensor 24. Then, the processor 36A determines whether or not the first fluctuation has occurred in the HVPS voltage and the second fluctuation has occurred in the measured value of the force sensor 24, within the predetermined period $T(\Delta t_1 + \Delta t_2)$.

Here, when the measured value of the force sensor 24 exceeds a specific third threshold Th3 (FIG. 6), the processor 36A determines that the second fluctuation has occurred in the measured value of the force sensor 24. The third threshold Th3 is, for example, a value obtained by adding a specific value to a measured value of a normal force sensor 24 at the time of treatment of a target site. Further, the third threshold Th3 corresponds to a second threshold according to the disclosure.

Even when the mechanical load applied to the ultrasound probe 22 is adopted as the second index value according to the disclosure as in the second embodiment described above, the same effects as those of the first embodiment described above are obtained.

Other Embodiments

Although the embodiments of the disclosure have been described above, the disclosure should not be limited only to the first and second embodiments described above.

In the first and second embodiments described above, the output of the high-frequency signal from the high-frequency output circuit 332 is stopped in steps S4, S11, and S18, but the disclosure is not limited thereto, and a configuration in which the output value of the high-frequency signal is reduced (the high-frequency power is reduced) may be adopted.

In the first and second embodiments described above, the HVPS voltage is adopted as the first index value according to the disclosure, but the disclosure is not limited thereto.

For example, the HF current, the HF voltage, the HF impedance, the HF resistance, or the phase difference between the phase signal of the HF current and the phase signal of the HF voltage may be adopted as the first index value according to the disclosure. At this time, the HF signal detection circuit 34 corresponds to the first detection circuit according to the disclosure. Further, the HF signal corresponds to the first detection signal according to the disclosure.

In the first and second embodiments described above, the US impedance or the mechanical load (measured value of the force sensor 24) applied to the ultrasound probe 22 is adopted as the second index value according to the disclosure, but the disclosure is not limited thereto.

For example, the US current or the US voltage may be adopted as the second index value according to the disclosure. At this time, the US signal detection circuit 32 corresponds to the second detection circuit according to the disclosure. Further, the US signal corresponds to a second detection signal according to the disclosure.

In the first and second embodiments described above, the treatment tools 2 and 2A are formed of a monopolar treatment tool using the external counter electrode plate, but the disclosure is not limited thereto. The treatment tools 2 and 2A may be formed of a bipolar treatment tool that causes each of a pair of gripping members for gripping the target site to function as a high-frequency electrode.

In the first and second embodiments described above, the configuration in which the ultrasound energy and the high-frequency energy can be applied to the target site is adopted, but the disclosure is not limited thereto.

For example, a configuration in which only the high-frequency energy is applied to the target site may be adopted.

Further, for example, a configuration in which, in addition to the high-frequency energy, thermal energy can be applied to the target site may be adopted. Here, "applying thermal energy to the target site" means transferring heat from a heater or the like to the target site.

In the first and second embodiments described above, the first high-frequency output processing is executed in the coagulation/incision mode, but the disclosure is not limited thereto, and a configuration in which the second high-frequency output processing is executed may also be adopted.

Further, the flow illustrating the control method executed by the processors 36 and 36A is not limited to the order of processing in the flowchart (FIG. 3) described in the first and second embodiments described above, and the order of processing may be changed within a consistent range.

According to a medical device, a control method, and a computer-readable storage medium according to the disclosure, the presence or absence of contact between an end effector and an electroconductive member such as a metal forceps can be detected with high accuracy, so that deterioration of treatment performance of a biological tissue can be suppressed.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A medical device comprising:
   a high-frequency power supply configured to output a high-frequency signal to an end effector, the end effector being configured to apply high-frequency energy to treat a biological tissue;

a first detection circuit configured to detect a first index value of an output state of the high-frequency signal;
a second detection circuit configured to detect a second index value of a mechanical load applied to the end effector; and
a processor configured to execute a first mode to reduce an output value of the high-frequency signal when a fluctuation of the first index value detected by the first detection circuit occurs and then a fluctuation of the second index value detected by the second detection circuit occurs within a predetermined time period, wherein the predetermined time period is a time from when the fluctuation of the first index value occurs until 3 ms-10 ms has elapsed, wherein:
the high-frequency power supply includes:
  a power supply main body configured to output power; and
  an output circuit configured to output the high-frequency signal by converting the power output from the power supply main body, and
the first detection circuit is configured to detect a voltage of the power supply main body as the first index value.

2. The medical device according to claim 1, wherein
the first detection circuit is configured to output a first detection signal by detecting the first index value,
the second detection circuit is configured to output a second detection signal by detecting the second index value, and
when a fluctuation of the first detection signal based on the fluctuation of the first index value occurs and a fluctuation of the second detection signal based on the fluctuation of the second index value occurs, the processor is configured to execute the first mode.

3. The medical device according to claim 1, wherein
in the first mode, when the fluctuation of the first index value and the fluctuation of the second index value occur, the processor is configured to stop an output of the high-frequency signal from the high-frequency power supply.

4. The medical device according to claim 3, wherein
in the first mode, the processor is configured to continue to stop the output of the high-frequency signal from the high-frequency power supply for a specific period, and the specific period has elapsed, the processor is configured to restart the output of the high-frequency signal from the high-frequency power supply.

5. The medical device according to claim 1, wherein
in the first mode, when one of the fluctuation of the first index value and the fluctuation of the second index value occurs and then another fluctuation of the fluctuation of the first index value and the fluctuation of the second index value occurs within a predetermined period, the processor is configured to reduce the output value of the high-frequency signal from the high-frequency power supply.

6. The medical device according to claim 1, further comprising:
an ultrasound power supply configured to output a drive signal to an ultrasound transducer configured to generate ultrasound energy for treating the biological tissue, wherein
the end effector is configured to apply the ultrasound energy to the biological tissue, and
the second detection circuit is configured to detect the second index value that is an indication of an output state of the drive signal by the ultrasound power supply.

7. The medical device according to claim 6, wherein
the second detection circuit is configured to detect, as the second index value, an ultrasound impedance based on a voltage value and a current value in the drive signal output from the ultrasound power supply.

8. The medical device according to claim 1, wherein
the second detection circuit is a force sensor configured to detect a mechanical load applied to the end effector as the second index value.

9. The medical device according to claim 1, wherein
when the first index value exceeds a first threshold, the processor is configured to determine that the fluctuation of the first index value occurs, and when the second index value exceeds a second threshold, the processor is configured to determine that the fluctuation of the second index value occurs.

10. The medical device according to claim 1, wherein
in the first mode, when at least one of the fluctuation of the first index value and the fluctuation of the second index value does not occur, the processor is configured to maintain an output of the high-frequency signal from the high-frequency power supply.

11. The medical device according to claim 1, wherein
the processor is configured to execute a second mode different from the first mode, according to a treatment mode for treating the biological tissue, and
in the second mode, when the first index value is monitored and the fluctuation of the first index value occurs, the processor is configured to reduce the output value of the high-frequency signal from the high-frequency power supply.

12. The medical device according to claim 11, wherein
in the second mode, when the fluctuation of the first index value occurs, the processor is configured to stop an output of the high-frequency signal from the high-frequency power supply.

13. The medical device according to claim 12, wherein
in the second mode, the processor is configured to continue to stop the output of the high-frequency signal from the high-frequency power supply for a specific period, and after completion of the specific period, the processor is configured to restart the output of the high-frequency signal from the high-frequency power supply.

14. The medical device according to claim 11, wherein
the treatment mode includes a combined treatment mode in which both coagulation and incision of the biological tissue are performed, and
when the treatment mode is the combined treatment mode, the processor is configured to execute the first mode.

15. The medical device according to claim 11, wherein
the treatment mode includes a single treatment mode in which only coagulation or incision of the biological tissue is performed, and
when the treatment mode is the single treatment mode, the processor is configured to execute the second mode.

16. A control method executed by a processor of a medical device, the control method comprising:
monitoring, as a first index value, a voltage of a power supply main body of a high-frequency power supply, the first index value being an indication of an output state of a high-frequency signal output to an end effector by converting power output from the power supply main body;
monitoring a second index value that is an indication of a mechanical load applied to the end effector; and reducing an output value of the high-frequency signal from the high-frequency power supply, when a fluctuation of the first index value occurs and then a fluctuation of the second index value occurs within a predetermined time period, wherein the predetermined time period is a time from when the fluctuation of the first index value occurs until 3 ms-10 ms has elapsed.

17. A non-transitory computer-readable storage medium for storing a control program, the control program causing a processor of a medical device to:

monitor, as a first index value, a voltage of a power supply main body of a high-frequency power supply, the first index value being an indication of an output state of a high-frequency signal output to an end effector by converting power output from the power supply main body;

monitor a second index value that is an indication of a mechanical load applied to the end effector; and reduce an output value of the high-frequency signal from the high-frequency power supply, when a fluctuation of the first index value occurs and then a fluctuation of the second index value occurs within a predetermined time period, wherein the predetermined time period is a time from when the fluctuation of the first index value occurs until 3 ms-10 ms has elapsed.

18. A medical device comprising:

a high-frequency power supply configured to output a high-frequency signal to an end effector, the end effector being configured to apply high-frequency energy to treat a biological tissue;

a first detection circuit configured to detect a first index value of an output state of the high-frequency signal;

a second detection circuit configured to detect a second index value of a mechanical load of an electroconductive member applied to the end effector; and a processor configured to execute a first mode to reduce an output value of the high-frequency signal when a fluctuation of the first index value detected by the first detection circuit occurs and a fluctuation of the second index value detected by the second detection circuit occurs within a predetermined time period, wherein the predetermined time period is a time from when the fluctuation of the first index value occurs until 3 ms-10 ms has elapsed, wherein:

the high-frequency power supply includes:

a power supply main body configured to output power; and an output circuit configured to output the high-frequency signal by converting the power output from the power supply main body, and the first detection circuit is configured to detect a voltage of the power supply main body as the first index value.

* * * * *